(12) United States Patent
Acker et al.

(10) Patent No.: US 7,305,988 B2
(45) Date of Patent: Dec. 11, 2007

(54) INTEGRATED VENTILATOR NASAL TRIGGER AND GAS MONITORING SYSTEM

(75) Inventors: Jaron M. Acker, Madison, WI (US);
Robert Q. Tham, Middleton, WI (US);
Andreas Tzanetakis, Madison, WI (US)

(73) Assignee: The General Electric Company, Schenectady, NY (US)

( * ) Notice: Subject to any disclaimer, the term of this patent is extended or adjusted under 35 U.S.C. 154(b) by 237 days.

(21) Appl. No.: 11/315,751

(22) Filed: Dec. 22, 2005

(65) Prior Publication Data

US 2007/0144518 A1 Jun. 28, 2007

(51) Int. Cl.
*A61M 11/00* (2006.01)
(52) U.S. Cl. ............... 128/204.18; 128/204.23
(58) Field of Classification Search ........... 128/207.18, 128/203.22, 204.18, 912, 204.23, 204.26, 128/206.11, 207.17
See application file for complete search history.

(56) References Cited

U.S. PATENT DOCUMENTS

| 4,745,925 | A |   | 5/1988  | Dietz   |            |
|-----------|---|---|---------|---------|------------|
| 4,989,599 | A | * | 2/1991  | Carter  | 128/207.18 |
| 5,005,571 | A |   | 4/1991  | Dietz   |            |
| 5,474,060 | A |   | 12/1995 | Evans   |            |
| 5,603,315 | A |   | 2/1997  | Sasso, Jr. |        |
| 6,655,385 | B1| * | 12/2003 | Curti et al. | 128/207.18 |
| 6,863,069 | B2| * | 3/2005  | Wood    | 128/207.18 |
| 2002/0017300 | A1 |  | 2/2002 | Hickle et al. |    |
| 2002/0029004 | A1 |  | 3/2002 | Starr et al. |     |
| 2005/0011523 | A1 |  | 1/2005 | Aylsworth et al. | |
| 2005/0121033 | A1 |  | 6/2005 | Starr et al. |     |

FOREIGN PATENT DOCUMENTS

EP  0 330 740 A2  9/1989

OTHER PUBLICATIONS

European Search Report, dated Apr. 3, 2007.

* cited by examiner

*Primary Examiner*—Steven O. Douglas
(74) *Attorney, Agent, or Firm*—Andrus, Sceales, Starke & Sawall, LLP

(57) ABSTRACT

An arrangement and method for detecting spontaneous respiratory effort of a patient receiving ventilatory support by a breathing circuit. The nasal cannula control system includes a nasal cannula assembly having two distinct lumens. A different pressure sensor is positioned to detect the pressure difference between each of the two lumens, thereby determining the differential pressure from within the patient's nostrils and within a breathing mask. The nasal cannula control system includes a gas sampling system such that the amount of a monitored gas discharged or exhaled by the patient can be monitored using the same nasal cannula assembly used to generate the differential pressure signal.

16 Claims, 6 Drawing Sheets

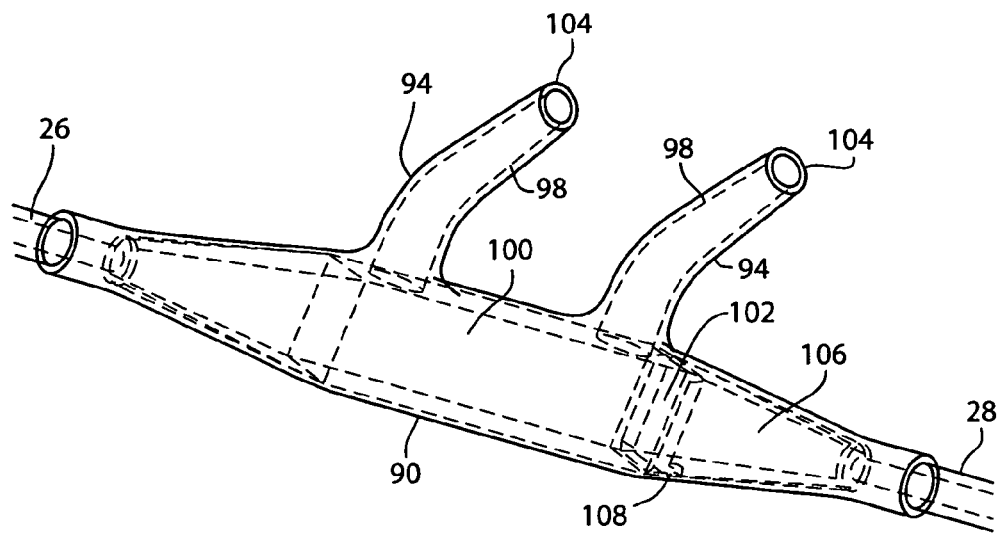
FIG. 5
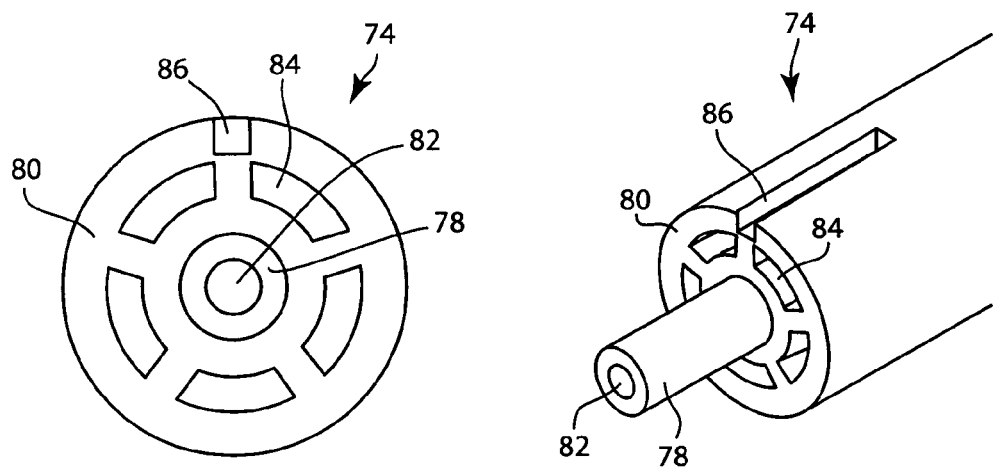
FIG. 6a
FIG. 6b

INTEGRATED VENTILATOR NASAL TRIGGER AND GAS MONITORING SYSTEM

FIELD OF THE INVENTION

The present invention relates to a medical device for providing medical gases to a patient. More specifically, the present invention relates to a nasal cannula control system that may provide supplemental medical gas to a patient while also performing triggering of ventilation support and the monitoring of an exhaled gas from a patient, such as carbon dioxide.

BACKGROUND OF THE INVENTION

Patients that have respiratory difficulties often must be placed on a mechanical ventilator. These difficulties may be pathological in nature or may be due to the fact that a patient is too weak or sedated to independently perform proper respiration functions. Often, the patient may be spontaneously attempting to breath, but not able to complete a full respiratory cycle. In these cases, mechanically assisted ventilation is provided. In mechanically assisted ventilation, a combination of pressure and/or flow sensors detects a patient's breath attempt. This detection triggers the delivery of a mechanical breath, which is provided in the inspiratory phase by the delivery of a pulse or plug of medical gases under a pressure that is sufficient to overcome the resistance of the patient's airway, thus filling the lungs. When this pulse of medical gas is discontinued, the natural compliance of the patient's chest wall forces the delivered breath out of the patient in an expiratory phase.

Often, mechanical ventilation is supplemented by an additional delivery of medical gas, such as oxygen or nitric oxide, to the patient. This additional gas may be supplied within the mixture of medical gases delivered during mechanical ventilation, or the supplemental oxygen may be delivered to the patient directly through the nostrils by the use of a nasal cannula. Additionally, a patient who is not on mechanical ventilation, but rather is spontaneously performing complete respiration cycles, may receive supplemental oxygen via a nasal cannula to increase the oxygen uptake by the lungs. In situations where a patient is receiving supplemental oxygen and/or mechanical ventilation, it is desirable to measure the end tidal carbon dioxide in the patient's exhaled breathing gases. This is a useful medical quantity as it is indicative of the patient's respiratory efficiency as well as a useful diagnostic tool for an attending clinician. The monitoring of end tidal $CO_2$ levels can provide the clinician with information regarding oxygen-carbon dioxide exchange, alveolar recruitment, and acid-base disorders.

In prior systems that utilize a non-invasive ventilation (NIV) mask for patient ventilation and also monitor $CO_2$ levels in the expired patient gases, leaks within the system cause diluting effects, thereby making $CO_2$ measurements at the Y-piece or in the expiratory limb difficult.

The efficiency of the mechanical ventilation of a patient may be increased by performing accurate triggering of the delivery of ventilator support in association with a patient's spontaneous breath attempt. Known ventilators and breathing circuits comprise a variety of flow and pressure sensors that produce signals to detect breathing effort by the patient and may trigger the ventilator to deliver a breath to the patient that is synchronous with those efforts. In known arrangements, the flow and/or pressure sensors are placed in the patient breathing circuit, in the patient breathing circuit interface, or in the ventilator.

One common method of mechanically ventilating a patient includes a non-invasive ventilation (NIV) breathing mask applied over the nose and mouth of a patient to deliver the ventilation gases to the patient. However, in this type of an arrangement, if the ventilator is delivering positive air pressure and the NIV mask is inadvertently pushed against the patient, the patient sensing mechanism will identify the resulting increase in pressure and interpret the increase as a patient's attempt to cycle the breath to expiration. This false identification would be due to the increased pressure in the face mask, resulting from the inadvertent compression of the face mask.

In another event, if a circuit leak occurs during the expiratory phase of the breath, the sensing mechanism would identify the resulting pressure change and interpret it as a patient's attempt to trigger a breath. Such a misinterpretation results in asynchrony between the ventilator and the patient's respiratory efforts, ultimately reducing the assistance provided to the patient. While leaks can occur anywhere in the circuit, a common location for leaks is between the patient/breathing circuit interface and the patient, which is typically where the face mask meets the patient's face.

Therefore, it is desirable in the field of medical gas delivery to patients to provide a nasal cannula and control system that provides effective patient triggering when used in conjunction with a mechanical ventilator. Further, it is desirable to provide a nasal cannula control system that is able to monitor the amount of a selected gas in the expiratory gas flow from the patient and provide a signal indicative of the sensed gas concentration.

SUMMARY OF THE INVENTION

In general, the present invention provides a nasal cannula and control system that provides carbon dioxide sampling and respiration monitoring, which may be used in conjunction with a mechanical ventilator. A nasal cannula is provided which may be used independently of a mechanical ventilator to provide supplemental medical gas, namely oxygen to a patient. The nasal cannula and control system of the present invention may also be utilized in conjunction with a mechanical ventilator to provide effective ventilator control and carbon dioxide sampling of the patient's expired gases.

An additional aspect of the nasal cannula and control system of the present invention comprises carbon dioxide sampling and monitoring by the control system with samples taken via the nasal cannula from the patient's nostrils. The sampling creates a steady state signal upon which the patient's respiratory effort signal rides in determining the detection of a patient's spontaneous breath attempt. Therefore, the present invention provides an efficient combination of carbon dioxide sampling and patient ventilation triggering from a sample taken from the patient airway.

BRIEF DESCRIPTION OF THE DRAWINGS

FIG. 5 is a perspective view of the nose piece of the nasal cannula used to sense differential pressure and monitor an exhaled gas from the patient;

FIG. 6a is a front view of one embodiment of the dual-lumen nasal cannula;

FIG. 6b is a perspective view of the dual-lumen nasal cannula;

DETAILED DESCRIPTION OF THE INVENTION

Figure 1:
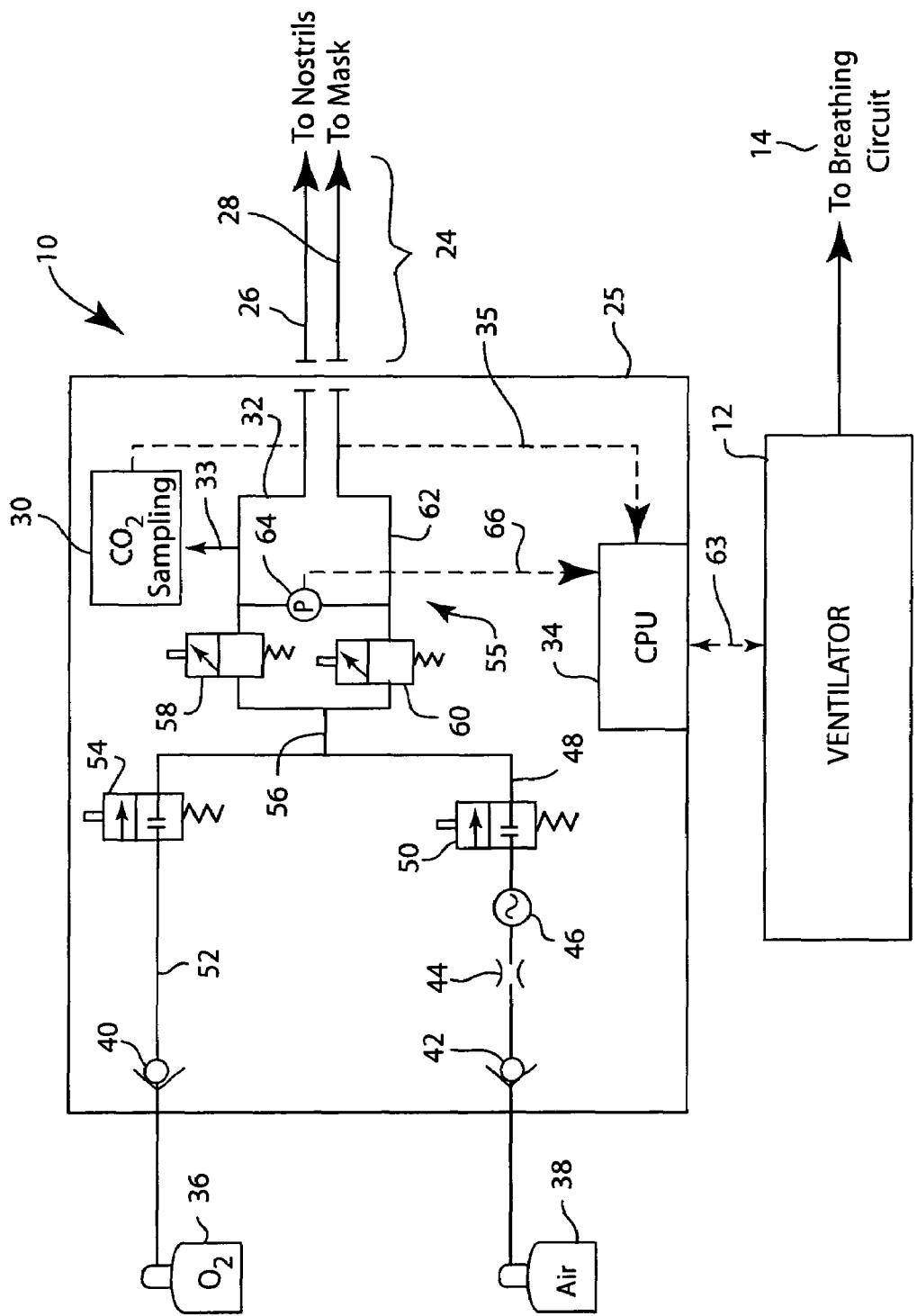
FIG. 1 is a schematic diagram of the nasal cannula assembly and control unit of the present invention.

Referring first to FIG. 1, a nasal cannula control system 10 is shown as used with a positive pressure ventilator 12. Although a positive pressure ventilator 12 is shown, it should be understood that the ventilator 12 could be of any type, such as an anesthesia, ICU or transport ventilator. Additionally, although the nasal cannula control system 10 is shown separate from the ventilator 12, the nasal cannula control system 10 could be incorporated directly into the ventilator 12.

The ventilator 12 delivers a supply of ventilation gas to a patient breathing circuit 14 to provide mechanical ventilation of the patient. In the embodiment of the invention shown in FIG. 2, the patient breathing circuit 14 includes a non-invasive ventilation (NIV) breathing mask 16 that is used to deliver gases to the patient 18. As illustrated, the breathing mask 16 covers both the nose and mouth of the patient 18 and forms a seal 20 with the patient along the outer peripheral edges of the breathing mask 16. The breathing mask 16 includes an inlet 22 that receives the pressurized gases from the ventilator 12 during the inspiratory phase of the patient breathing cycle and provides an outlet path for the exhaled gases from the patient to the ventilator during the expiratory phase of the breathing cycle.

Figure 2:
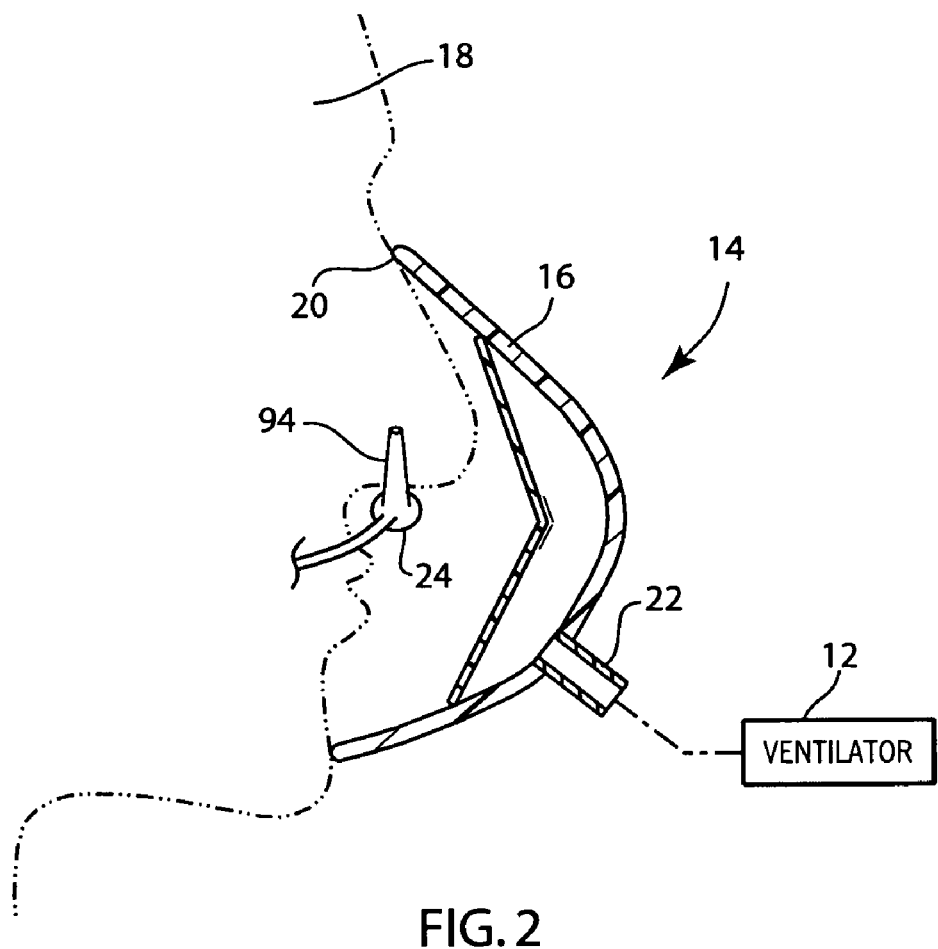
FIG. 2 is a side section view of an NIV face mask and nasal cannula used during ventilation of a patient.

As illustrated in FIG. 2, a nasal cannula 24 is positioned in the nostrils of the patient to either deliver a flow of gases to the patient or to sense the pressure within the nostrils of the patient and within the mask 16 in the manner to be described below.

Referring back to FIG. 1, the nasal cannula control system 10 includes a self contained monitoring unit 25 that interfaces with the nasal cannula assembly 24 that includes two separate lumens. The nasal cannula assembly 24 includes a nasal lumen 26 that is in pneumatic communication with the patient's nostrils and a mask lumen 28 that is in pneumatic communication with the interior of the patient's breathing mask. Although the two lumens 26, 28 are described as extending to defined areas, namely the nostrils and breathing mask, the lumens 26, 28 could terminate at other locations depending upon the specific patient and the configuration of the patient breathing circuit 14. The nasal cannula control system 10 utilizes the combination of the nasal lumen 26 and the mask lumen 28 to monitor the pressure within the patient mask and nostrils of the patient, as well as to monitor an exhaled gas from the patient, such as the carbon dioxide concentration within the nasal canal of the patient.

As illustrated in FIG. 1, a $CO_2$ sampling system 30 is in pneumatic communication with the nasal lumen 26 through the gas line 32 and a withdrawal conduit 33. Although the present invention is shown and described as including a $CO_2$ sampling system 30, it should be understood that the $CO_2$ sampling system 30 could be replaced by sampling systems for detecting other exhaled gases. As an example, the $CO_2$ sampling system 30 could be replaced by a sampling system that detects exhaled gases such as nitric oxide, an inhaled anesthetic agent, oxygen, nitrous oxide or any other exhaled gas that may be of concern during the treatment of the patient. Throughout the remaining disclosure, the invention will be described as monitoring for the presence of $CO_2$. However, it should be understood that the monitoring of other exhaled gases is within the scope of the present invention.

The $CO_2$ sampling system 30 includes a $CO_2$ pump (not shown) that draws a measurement flow of gas from the nostrils of the patient through the nasal lumen 26, the gas line 32 and the withdrawal conduit 33. The $CO_2$ sampling system 30 is operable to monitor the carbon dioxide content in the patient's expired breathing gases using a conventional analyzing system. As an example, the analyzing system within the $CO_2$ sampling system 30 may be performed by a capnometer, which is an infrared detector that is commonly used in medical applications to analyze the carbon dioxide content to monitor a patient's lung exchange. The $CO_2$ sampling system 30 is in communication with a control unit 34 of the nasal cannula control system 10. The control unit 34 can communicate with the ventilator 12 over the communication line 63 to provide the carbon dioxide sampling measurement to the ventilator 12 as desired. Upon receiving the carbon dioxide sampling measurement, the ventilator 12 can either adjust its operation or generate an alarm signal as desired. The use of the $CO_2$ sampling system 30 within the nasal cannula control system 10 allows the $CO_2$ monitoring function to be removed from the ventilator 12. Further, since the $CO_2$ sampling system 30 withdraws the measurement gas flow directly from the nostrils of the patient, the $CO_2$ measurement provides greater accuracy as compared to prior art systems that sample $CO_2$ either within the patient interface, breathing circuit or within the ventilator 12.

Although the $CO_2$ sampling system 30 is shown in the preferred embodiment of the invention as drawing the measurement gas flow from the nasal lumen 26, it should be understood that the sampling system could also draw the measurement gas flow from the mask lumen 28. It is believed that drawing the measurement gas flow from the nostrils of the patient will lead to a more accurate $CO_2$ measurement due to the more direct gas withdrawal from the patient. However, utilizing the mask lumen 28 would also allow for $CO_2$ sampling and measurement.

Referring back to FIG. 1, the monitoring unit 25 of the nasal cannula control system 10 is coupled to an oxygen supply 36 and a fresh air supply 38. The monitoring unit includes a pair of check valves 40, 42 that prevent the reverse flow of gas from the monitoring unit 25. The air supply 38 passes through a pneumatic resistor 44 to ensure that the flow rate of pressurized air 38 is relatively low. In an alternate embodiment, a pump 46 can be included in the air supply line 48 in the place of the pressurized air source 38. An air flow valve 50 is positioned in the air supply line 48 to control the flow of the air through air line 48 and allows for adjustable flow rates of air.

The oxygen supply 36 is received in a oxygen flow line 52, which also includes a flow valve 54 for regulating the flow of oxygen. The pair of flow valves 50, 54 are independently operable such that either or both of oxygen supply 36 and air supply 38 can be directed to the patient.

The flow of oxygen and air are both supplied to a purging and sensing circuit 55 by conduit 56, which separates and supplies the flow of gas to a first purge valve 58 and a second purge valve 60. As illustrated, the first purge valve 58 is in communication with the nasal lumen 26 through gas line 33, while the second purge valve 60 is in communication with the mask lumen 28 through gas line 62.

During operation of the nasal cannula control system 10, either one or both of the nasal lumen 26 and the mask lumen 28 can be purged to flush patient fluids, such as mucus, by using either the oxygen supply 36 or the air supply 38. The nasal cannula control system 10 utilizes the differential pressure sensed by the pressure sensor 64 to determine whether the nasal lumen 26 or the mask lumen 28 has become blocked, such by mucous or other fluid. If control unit 34 detects the a differential pressure change that signals an occluded lumen, the control unit 34 will signal the ventilator 12. The ventilator 12 can provide a message to the nasal cannula control system 10 along communication line 63 to begin the purging operation in synchronization with a specific portion of the patient breathing cycle. Typically, the purging is timed to occur during either the beginning of the inspiratory phase or the beginning of the expiratory phase to allow proper monitoring during the remaining portions of the breathing cycle.

During the purging cycle, the pump within the $CO_2$ sampling system 30 is initially turned off to discontinue drawing any measurement gas flow from the patient. Once the $CO_2$ pump has been turned off, if the nasal lumen 26 is to be purged, the first purge valve 58 is opened. Once the purge valve 58 has been opened, the corresponding flow valve 50 or 54 is opened to supply either the pressurized oxygen or air to the nasal cannula 26. After a brief period of time, the purge valve 58 is closed and the purge valve 60 opened to purge the mask lumen 28. Once both the nasal lumen 26 and the mask lumen 28 have been purged, both of the purge valves 58, 60 are closed and the $CO_2$ sampling system 30 begins operation the capnometer pump.

Referring back to FIG. 1, the nasal cannula control system 10 includes a differential pressure sensor 64 that is connected between the gas line 32 and the gas line 62. Thus, the differential pressure sensor 64 is able to measure the differential pressure existing between the nasal lumen 26 and the mask lumen 28. The use of the differential pressure between the nasal lumen 26 and the mask lumen 28 allows the nasal cannula control system 10 to detect respiratory events, such as exhalation or inhalation, and generate a triggering signal that is relayed to the ventilator 12 through the communication line 63.

During normal ventilation by the ventilator 12, the pair of purge valves 58, 60 are closed and the differential pressure sensor 64 measures the pressure difference between the nasal lumen 26 and the mask lumen 28. The pressure difference between the nasal lumen 26 and the mask lumen 28 is offset by the negative pressure created by the $CO_2$ sampling system 30 in drawing the measurement gas flow from the patient through the nasal lumen 26. The offset created by the $CO_2$ sampling system 30 can be monitored and subtracted from the measured signal detected by the differential pressure sensor 64. The differential pressure sensor 64 is in communication with the control unit 34 through the communication line 66. In this manner, the control unit 34 can monitor for changes in the differential pressure, which is indicative of the various phases within the patient's breath cycle.

At any time during operation of the system, the differential pressure sensor 64 can be calibrated, or "zeroed", by opening the pair of purge valves 58, 60. When the purge valves are opened, the differential pressure sensor is effectively short circuited. At this time, the output from the differential pressure sensor 64 is set to zero to effectively remove any offsets in the signal from the sensor.

Figure 4:
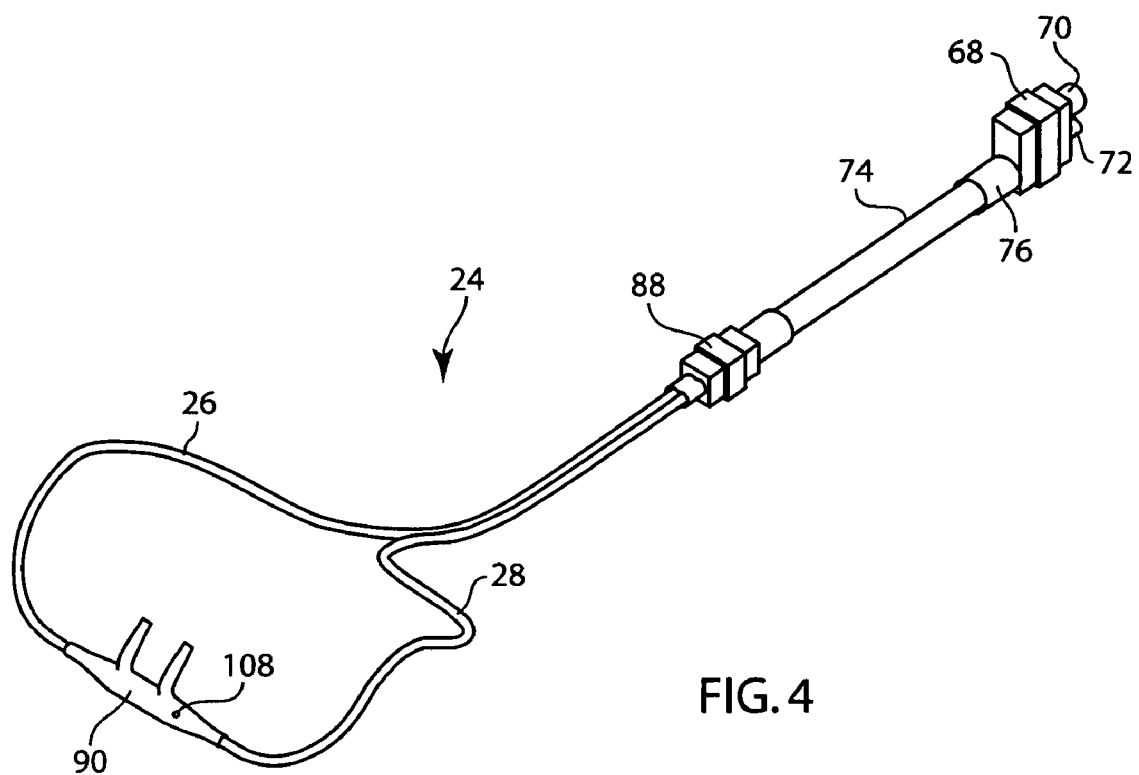
FIG. 4 is a perspective view of the nasal cannula assembly of the present invention.

Referring now to FIG. 4, thereshown is the nasal cannula assembly 24 of the present invention. The nasal cannula assembly 24 includes a connector 68 having a first inlet port 70 and a second inlet port 72. The inlet ports 70, 72 interface with the monitoring unit of nasal cannula control system to ensure that the nasal lumen 26 and mask lumen 28 are properly connected to the nasal cannula control system. The connector 68 is coupled to a dual-lumen cannula 74 through the outlet port 76.

FIGS. 6a and 6b illustrate a preferred embodiment of the dual-lumen cannula 74, although other embodiments are contemplated as being within the scope of the present invention. As illustrated in FIG. 6b, the dual-lumen cannula includes an inner lumen 78 and an outer lumen 80 that are generally coaxial with each other. The inner lumen 78 includes a center passageway 82 while the outer lumen 80 includes a series of flow passageways 84. In the embodiment illustrated in FIG. 6b, an alignment notch 86 is included in the outer lumen 80 to aid in proper alignment of the lumen within the connector 68. As can be understood in FIGS. 6a and 6b, the dual-lumen cannula 74 allows for two separate flows of gas to be delivered to the channel interface 88 shown in FIG. 4. The channel interface 88 receives both the nasal lumen 26 and the mask lumen 28 and separates the two lumens to interface with the inner and outer lumens 78, 80.

Although the FIGS. 6a and 6b illustrate a dual-lumen cannula, it is contemplated that a tri-lumen cannula could also be utilized to allow for independent purging of the nostrils.

Figure 3:
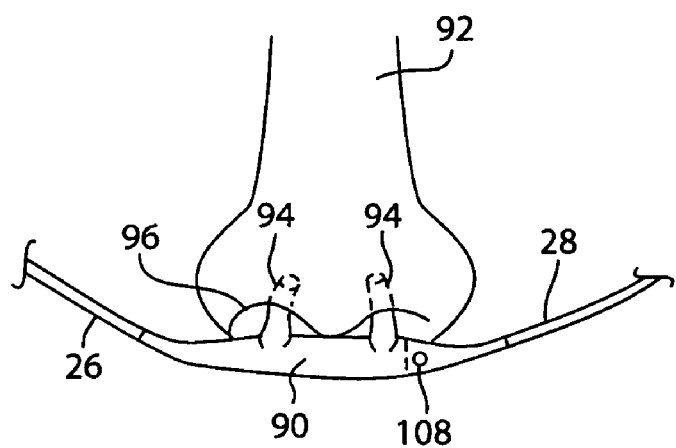
FIG. 3 is a front view illustrating the positioning of the nose piece of the nasal cannula assembly within the nostrils of the patient.

Referring now to FIGS. 3 and 4, the nasal cannula assembly 24 includes a patient nose piece 90 designed to be received within the nose 92 of the patient. As illustrated in FIG. 3, the nose piece 90 includes a pair of nasal stems 94 that extend into the patient's nostrils 96. The nose piece 90 receives both the nasal lumen 26 and the mask lumen 28.

Referring now to FIG. 5, each of the nasal stems 94 includes an open passageway 98 in communication with a central chamber 100. The central chamber 100 is defined at one end by a separating wall 102 and is open at the other end to pneumatically communicate with the nasal lumen 26. Thus, the pressure at each end 104 of the pair of nasal stems 94 is communicated to the nasal lumen 26 through the open passageways 98 and the central chamber 100. In this manner, the pressure within the patient's nostrils can be sensed using the nasal lumen 26.

In addition to the central chamber 100, the nose piece 90 includes a separate, isolated side chamber 106 defined at one end by the separating wall 102. The side chamber 106 is in pneumatic communication with the mask lumen 28. The outer wall of the side chamber 106 includes an opening 108 that allows the pressure within the patient mask to be communicated into the side chamber 106. The side chamber 106 is completely isolated from the pressure within the central chamber 100, such that the nasal lumen 26 communicates the pressure within the nostrils of the patient while the mask lumen 28 communicates the pressure within the patient mask 16.

Referring back to FIG. 1, the gas line 32 within the nasal cannula control system 10 is in pneumatic connection with the patient's nostrils and gas line 62 is in pneumatic connection with the air outside the nose piece 90, but within the patient's mask. Thus, the differential pressure between lines 32 and 62 is representative of a differential pressure between the patient's nostrils and the patient mask. This differential pressure is used as the triggering mechanism to detect a patient's spontaneous breath attempt. The detection of the patient's spontaneous breath attempt is relayed from the control unit 34 to the ventilator 12.

During monitoring of the patient, the differential pressure sensor 64 continuously monitors the differential pressure between the nasal lumen 26 and the mask lumen 28. Since the nasal lumen 26 is positioned within the nostrils of the patient, an actual breathing attempt by the patient will cause a change in the differential pressure between the nasal lumen 26 and the mask lumen 28. Specifically, the pressure within the nasal lumen 26 will fall relative to the pressure within the mask lumen 28. If the differential pressure sensor 64 detects this change in the differential pressure, the detected pressure change causes the control unit 34 to signal the ventilator 12 to begin the inspiration support phase.

Alternatively, if the pressure within the nasal lumen 26 increases relative to the pressure within the mask lumen 28, this change in the differential pressure indicates that the patient has begun exhaling. Upon detection of the change in the pressure differential, the control unit 34 signals the ventilator 12 to begin the expiration phase of the breathing cycle.

Figure 7:
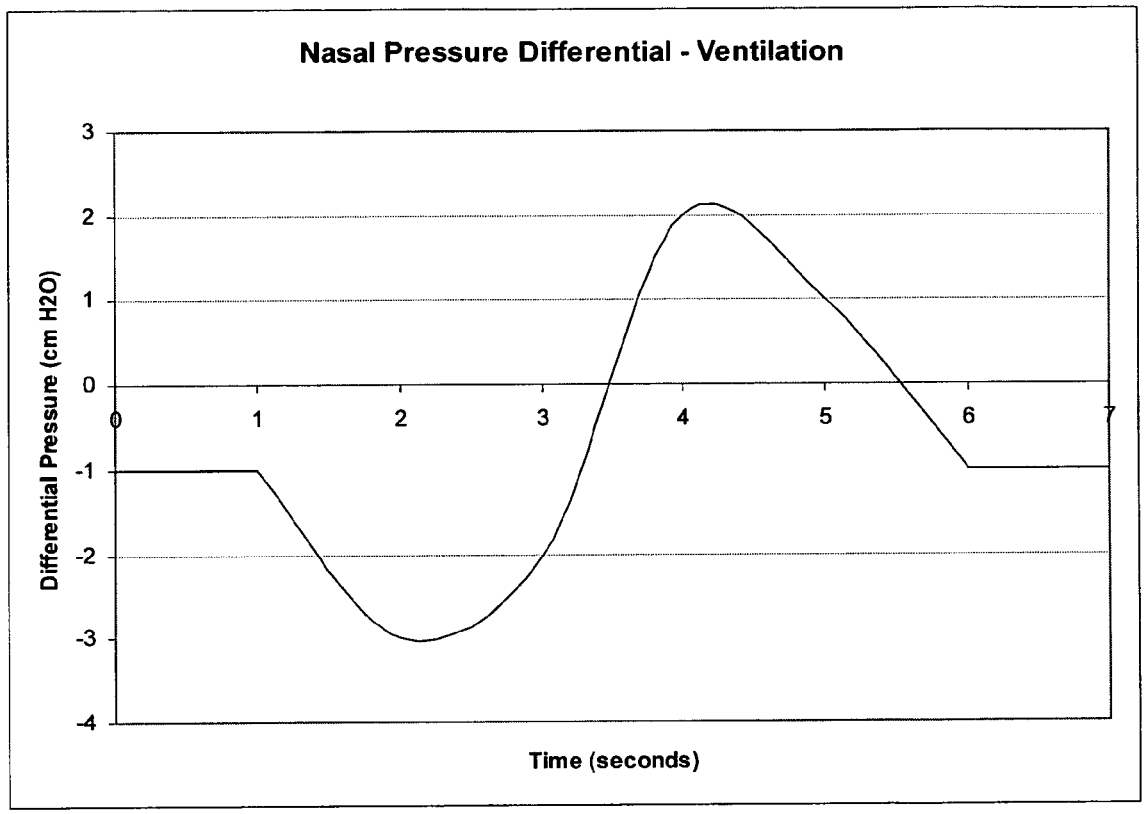
FIG. 7 is a graph of a patient's nasal pressure differential over the course of a respiratory cycle while a sample is being removed for $CO_2$ monitoring.

Referring now to FIG. 7, FIG. 7 is a graph depicting the nasal pressure differential while a patient is receiving mechanical ventilation. There is a constant offset of −1 cm $H_2O$ as a result of the pump in the $CO_2$ sampling system creating a measurement gas flow out of the nasal lumen 26. This pressure change is the result of laminar flow through the nasal cannula 24. At one second, the differential pressure dips below −1 cm. $H_2O$. This is when the control unit 34 will signal the positive pressure ventilator 12, via the communications link 63, that the patient is inhaling. The ventilator 12 will begin the delivery of positive pressure in an inspiration support phase. At 2.25 seconds, the differential pressure goes back above −1 cm $H_2O$ and the control unit 34, via the communications link, notifies the ventilator 12 that the patient has begun to exhale. The ventilator 60 will then start to provide pressure support for the expiratory cycle. Often this expiratory support will be the discontinuation of the positive pressure supplied during the inspiratory support phase. However, the expiratory support may include the application of positive end expiratory pressure, also known as PEEP therapy, to decrease airway resistance and promote gas exchange within the patient's lungs.

Although the nasal cannula control system 10 shown and described in the Figures has been discussed as being particularly useful in monitoring a pressure differential between the patient's nasal passages and within a breathing mask to signal the beginning of the inspiratory and expiratory phases of the breathing cycle, the nasal cannula assembly may also be used separate from the operation of the mechanism ventilator 12, such as for post-ventilation oxygen therapy. During post-ventilation oxygen therapy, the clinician can set a constant oxygen flow rate and the system 10 will deliver the required oxygen to the patient. Specifically, the nasal cannula control system 10 will turn off the capnometer pump that forms part of the $CO_2$ sampling system 30 and open the purge valve 58. The flow valve 54 will then be opened the desired amount to provide the requested flow of oxygen 36 to the patient. The differential pressure sensor 64 will monitor the flow of oxygen through the cannula 24 as a laminar flow element, since the mask lumen 28 will not include any flow of gas.

Figure 8:
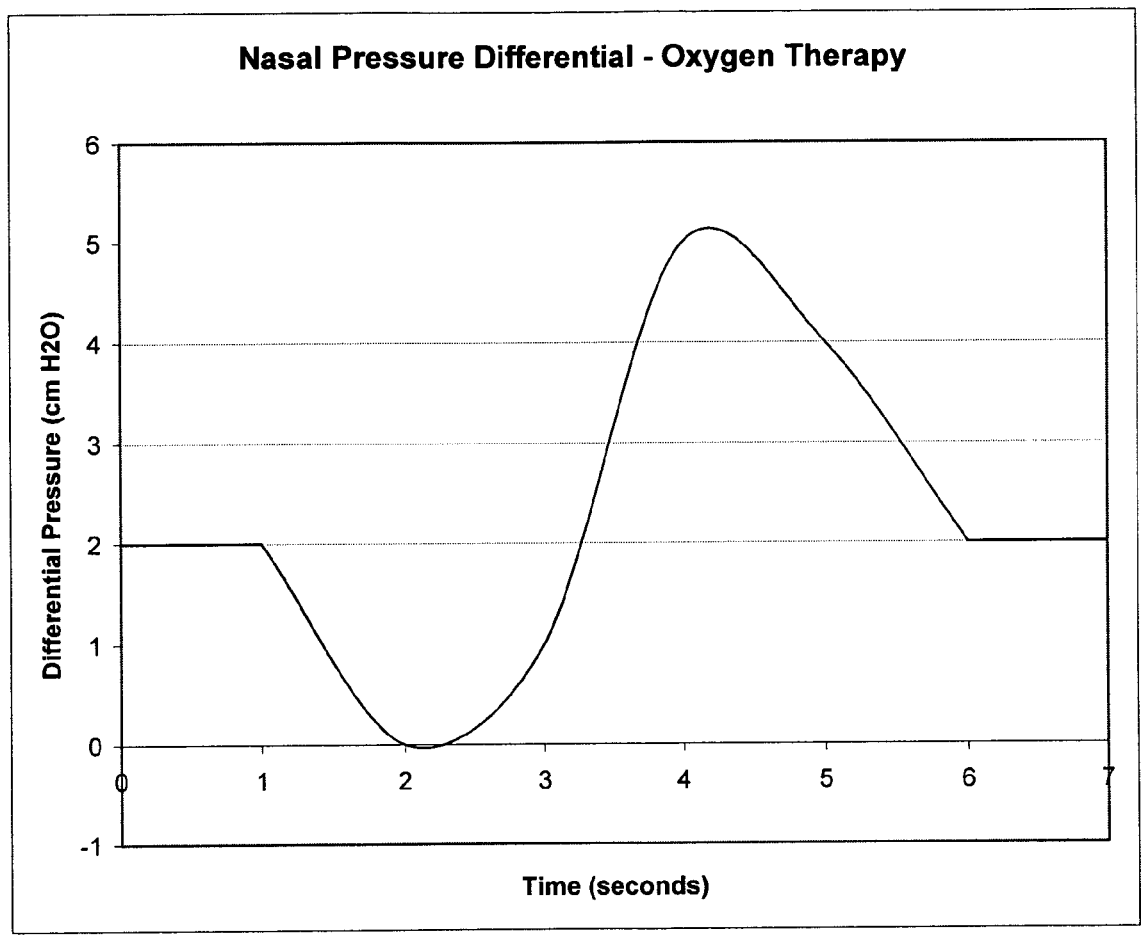
FIG. 8 is a graph of the patient's nasal pressure differential when the patient is on oxygen therapy over the course of a respiratory cycle.

Referring now to FIG. 8, thereshown is a graph of the nasal pressure differential measured by the pressure transducer 64 while the patient is receiving oxygen therapy. The graph shows a similar laminar flow present within the nasal cannula during post-ventilator oxygen therapy as was seen during the provision of mechanical ventilation assistance. As illustrated in FIG. 8, the differential pressure is offset a positive to 2 cm $H_2O$ because of the positive flow of gas traveling toward the patient from the oxygen supply. The respiratory rate for the patient can be measured using the differential pressure signal supplemented by the constant offset signal caused by the oxygen flow delivered to the patient during oxygen therapy.

During typical ventilation, the purge valves 58, 60 are closed and the differential pressure sensors 64 measure the pressure difference between the two lumens 26,28. During normal ventilation, the pump within the $CO_2$ sampling system 30 creates a negative pressure to draw a measurement gas flow from within the patient's nostril through the nasal lumen 26 and into the $CO_2$ sampling system 30. The $CO_2$ sampling system 30 includes a measuring device that determines the amount of carbon dioxide within the exhale gases of the patient and provides this signal to the control unit 34. Thus, the single nasal cannula assembly 24 can be utilized for not only monitoring the pressure differential between the patient's nostrils and the face mask, but also for monitoring the carbon dioxide exhaled by the patient.

We claim:

1. A nasal cannula control system for use in connection with a ventilator supplying ventilation gas to a patient through a patient interface, the system comprising:
    a control unit in communication with the ventilator;
    a nasal cannula assembly including a first lumen in pneumatic communication with the patient's airway and a second lumen in pneumatic communication with an area enclosed by the patient interface;
    a differential pressure sensor positioned to determine the differential pressure between the first lumen and the second lumen, wherein the differential pressure sensor is in communication with the control unit; and
    a gas sampling system in pneumatic communication with the first lumen, wherein the gas sampling system is operable to draw a measurement gas flow from a patient's airways through the first lumen,
    wherein the gas sampling system is operable to determine the gas concentration in the measurement gas flow and provides the gas measurement to the control unit.

2. The nasal cannula control system of claim 1 wherein the gas sampling system includes a pump operable to draw the measurement gas flow from the patient through the first lumen.

3. The nasal cannula control system of claim 1 wherein the control unit uses the differential pressure to determine a respiratory event.

4. The nasal cannula control system of claim 1 wherein the nasal cannula assembly includes a nose piece that receives both the first lumen and the second lumen, wherein the nose piece is receivable in the patient's nostrils such that the first lumen is in pneumatic communication with the patient's nostril.

5. The nasal cannula control system of claim 1 further comprising:
    a flushing gas supply in communication with both the first lumen and the second lumen;
    a first purge valve positioned between the flushing gas supply and a first lumen; and
    a second purge valve positioned between the flushing gas supply and the second lumen,
    wherein the first and second purge valves are selectively opened to provide the flushing gas supply to the first and second lumens to flush the first and second lumens.

6. The nasal cannula control system of claim 1 wherein the nasal cannula assembly includes a cannula section including an inner lumen and an outer lumen coaxial with the inner lumen.

7. The nasal cannula control system of claim 4 wherein the patient interface is a face mask such that the second lumen is in pneumatic communication with the area enclosed by the face mask.

8. The nasal cannula control system of claim 1 wherein the gas sampling system detects the concentration of carbon dioxide within the measurement gas flow.

9. A nasal cannula control system for use in connection with a ventilator supplying ventilation gas to a patient through a patient interface, the system comprising:
   the control unit in communication with the ventilator;
   a nasal cannula assembly including a first lumen in pneumatic communication with the patient's airway and a second lumen in pneumatic communication with an area enclosed by the patient interface;
   a differential pressure sensor positioned to determine the differential pressure between the first lumen and the second lumen, wherein the differential pressure sensor is in communication with the control unit; and
   a gas sampling system in pneumatic communication with the nasal cannula assembly, wherein the gas sampling system is operable to draw a measurement gas flow from the patient's airway through the nasal cannula assembly and determine a gas concentration in the measurement gas flow and provide the gas measurement to the control unit,
   wherein the control unit is operable to determine a respiratory event based upon the differential pressure and communicate the respiratory event to the ventilator.

10. The nasal cannula control system of claim 9 wherein the gas sampling system includes a pump operable to draw the measurement gas flow from the patient through the first lumen.

11. The nasal cannula control system of claim 9 wherein the gas sampling system detects the presence of carbon dioxide within the measurement gas flow.

12. The nasal cannula control system of claim 9 wherein the patient interface is a face mask such that the second lumen is in pneumatic communication with the area enclosed by the face mask.

13. The nasal cannula control system of claim 12 wherein the nasal cannula assembly includes a nose piece that receives both the first lumen and a second lumen, wherein the nose piece is receivable in the patient's nostrils such that the first lumen is in pneumatic communication with the patient's nostrils.

14. The nasal cannula control system of claim 9 further comprising:
   a flushing gas supply in communication with both the first lumen and the second lumen;
   a first purge valve positioned between the flushing gas supply and a first lumen; and
   a second purge valve positioned between the flushing gas supply and the second lumen,
   wherein the first and second purge valves are selectively opened to provide the flushing gas supply to the first and second lumens to flush the first and second lumens.

15. A nasal cannula for use in providing a flow of therapeutic gas to a patient in need of respiratory assistance, the nasal cannula comprising:
   a nose piece including a plurality of nasal stems for insertion into each nostril of a patient;
   a central chamber contained with the nose piece and in fluid connection with the pair of nasal stems;
   a first lumen in fluid communication with the central chamber;
   a second pneumatic chamber contained within the nose piece and isolated from the central chamber;
   a sampling port disposed in the nose piece and in communication with the second pneumatic chamber; and
   a second lumen in fluid communication with the second pneumatic chamber, wherein the pressure within the first lumen is the pressure within the patient's nostrils and the pressure in the second lumen is the pressure external to the nose piece.

16. The nasal cannula of claim 15 further comprising a connection means for connecting the first and second lumen to a controller, wherein the connection means is distinctly keyed such that the first and second lumen may only be connected in a single configuration.

* * * * *